United States Patent
Boyaval et al.

(10) Patent No.: US 12,303,677 B2
(45) Date of Patent: May 20, 2025

(54) HYBRID DRUG DELIVERY DEVICES WITH OPTIONAL GRIP PORTION AND RELATED METHOD OF PREPARATION

(71) Applicant: AMGEN INC., Thousand Oaks, CA (US)

(72) Inventors: Margaux Frances Boyaval, Newbury Park, CA (US); Brian Stonecipher, Newbury Park, CA (US); Avon Kuo, San Jose, CA (US); Lisa Nugent, Malibu, CA (US)

(73) Assignee: AMGEN INC., Thousand Oaks, CA (US)

( * ) Notice: Subject to any disclaimer, the term of this patent is extended or adjusted under 35 U.S.C. 154(b) by 1013 days.

(21) Appl. No.: 17/256,241

(22) PCT Filed: Jul. 11, 2019

(86) PCT No.: PCT/US2019/041322
§ 371 (c)(1),
(2) Date: Dec. 28, 2020

(87) PCT Pub. No.: WO2020/023220
PCT Pub. Date: Jan. 30, 2020

(65) Prior Publication Data
US 2021/0260279 A1 Aug. 26, 2021

Related U.S. Application Data

(60) Provisional application No. 62/702,785, filed on Jul. 24, 2018.

(51) Int. Cl.
*A61M 5/42* (2006.01)
*A61M 5/142* (2006.01)
(Continued)

(52) U.S. Cl.
CPC .......... *A61M 5/425* (2013.01); *A61M 5/1626* (2013.01); *A61M 5/3202* (2013.01); *A61M 5/14248* (2013.01); *A61M 2209/088* (2013.01)

(58) Field of Classification Search
CPC ... A61M 5/425; A61M 5/3204; A61M 5/3202
See application file for complete search history.

(56) References Cited

U.S. PATENT DOCUMENTS 6,537,242 B1 * 3/2003 Palmer ............. A61M 37/0015
600/583
2003/0229308 A1 * 12/2003 Tsals ....................... A61M 5/20
604/116

(Continued)

FOREIGN PATENT DOCUMENTS

JP 2005087519 A 4/2005
WO WO-2011156373 A1 12/2011

OTHER PUBLICATIONS

International Search Report and Written Opinion for International Patent Application No. PCT/US2019/041322, dated Dec. 13, 2019.

*Primary Examiner* — Jenna Zhang
(74) *Attorney, Agent, or Firm* — MARSHALL, GERSTEIN & BORUN LLP; Michael P. Furmanek

(57) ABSTRACT

Drug delivery devices are described that provide hybrid forms with optional gripping functionalities. For example, the devices can include a grip portion on a skin contact surface with a release liner disposed thereon. A user can operate the devices with the release liner disposed on the grip portion or can remove the release liner so that the grip portion is able to aid users in orienting and supporting the device during an injection operation.

10 Claims, 7 Drawing Sheets

(51) Int. Cl.
*A61M 5/162* (2006.01)
*A61M 5/32* (2006.01)

(56) References Cited

U.S. PATENT DOCUMENTS

2014/0163526 A1* 6/2014 Cabiri ................... A61M 5/425
                                                    604/513
2015/0258284 A1* 9/2015 Fenster ............... A61M 5/3205
                                                    604/115

* cited by examiner

HYBRID DRUG DELIVERY DEVICES WITH OPTIONAL GRIP PORTION AND RELATED METHOD OF PREPARATION

CROSS-REFERENCE TO RELATED APPLICATION

This is the United States national phase of International Patent Application No. PCT/US19/41322, filed Jul. 11, 2019, which claims priority to U.S. Provisional Patent Application No. 62/702,785, filed Jul. 24, 2018, the entire contents of each of which are hereby incorporated by reference herein.

FIELD OF THE DISCLOSURE

The present disclosure generally relates to drug delivery devices.

BACKGROUND

Drugs can be administered through the use of drug delivery devices such as autoinjectors or on-body injectors. Autoinjectors and on-body injectors may be used to help automate the injection and delivery or administration process, thereby simplifying the process for certain patient groups or sub-groups for which use of the syringe/vial combination or pre-filled syringe systems would be disadvantageous, whether because of physiological or psychological barriers, form factors, or ergonomic considerations.

Even after receiving specified training in the use of such devices, however, some patients and/or caregivers can experience challenges while using autoinjectors and/or on-body injectors. Such challenges may relate to placement of the device on the person, holding the device during an injection operation, and/or removing the device after use.

Specifically, conventional autoinjectors can have an elongate, high-profile housing that requires a user to position and hold the housing through an entire injection operation without additional aid. Conversely, conventional on-body injectors can have a low-profile housing with adhesive extending across a bottom surface thereof so that the housing can be adhered to the skin of the patient for hands-free operation.

SUMMARY

In accordance with some example aspects, drug delivery devices are described herein that include a housing having a bottom wall with a generally planar skin contact surface and an opening extending therethrough. The devices further include drug delivery components disposed within the housing that include a needle that has a storage position within the housing and an injection position extending through the opening of the bottom wall. Further, a tacky portion of the bottom wall is configured to grip skin of a user and a release liner is disposed over at least a portion of the tacky portion. The drug delivery components have a first potential operation state with the release liner disposed over the tacky portion and a second potential operation state with release liner removed to expose the tacky portion.

According to some forms, the housing extends along a longitudinal axis that is generally perpendicular to the skin contact surface and the drug delivery components are disposed in the housing such that at least a plurality of the drug delivery components are disposed in a generally stacked relation along the longitudinal axis.

With this housing configuration, some versions can include one or more of the following aspects: the bottom wall can have a dimension that extends thereacross that is between about one half and two thirds of a height of the housing along the longitudinal axis; the housing can include a transparent portion that provides visibility to drug delivery components disposed within the transparent portion; the housing can include an inner tubular portion that has one or more of the delivery components disposed therein aligned with the opening in the bottom wall and an outer wall spaced from the inner tubular portion in a direction perpendicular to the longitudinal axis; the inner tubular portion can extend to the bottom wall at an end thereof, the end having a tapered or bulleted configuration extending to edges of the opening of the bottom wall; the tacky portion can have an annular configuration that extends around the opening in the bottom wall.

Further, forms having such a housing configuration can also include a cap that is removably coupled to the housing to cover the skin contact surface of the bottom wall. The cap can further include a needle shield that is sized to extend through the opening in the bottom wall to engage the needle with the cap coupled to the housing and/or a sidewall that extends generally parallel to the longitudinal axis of the housing, where the release liner can include an outwardly protruding tab and the sidewall of the cap can include a gap therein sized to receive the tab of the liner therethrough with the cap coupled to the housing.

According to other forms, the housing can have a low profile with the drug delivery components distributed along a horizontal plane within the housing.

With this housing configuration, some versions can include one or more of the following aspects: the housing can include a raised ridge that extends along an upper surface thereof for manipulation of the housing by a user, where the raised ridge can optionally include at least one of an actuation button of the drug delivery components or a window providing visibility to one or more of the drug delivery components within the housing; the tacky portion can cover between about one fourth and one half of the skin contact surface; the tacky portion can have an annular configuration that extends around the opening in the bottom wall and the release liner can include an opening that extends therethrough that is configured to align with the opening in the bottom wall with the release liner disposed over the tacky portion; or the device can include a removable needle shield that is configured to be inserted through the opening in the bottom wall to engage the needle.

In an additional aspect, the tacky portion can be spaced from the opening in the bottom wall. With such a configuration, the release liner can be spaced from the opening in the bottom wall when disposed over the tacky portion or the release liner can cover the opening in the bottom wall when disposed over the tacky portion and the liner can be partially removable from the skin contact surface to expose the opening in the bottom wall in the first potential operation state.

In other aspects, the drug delivery device can include a removable needle shield configured to be inserted through the opening in the bottom wall to engage the needle and/or a septum extending over the opening in the bottom wall.

In accordance with other example aspects, the present disclosure related to a method of preparing a drug delivery device prior to injecting a patient with a drug, the method comprising providing a housing having a bottom wall with a generally planar skin contact surface and an opening extending therethrough, the bottom wall having a tacky portion. The method further includes disposing drug delivery components including a needle within the housing. The method further includes disposing a release liner over at least a portion of the tacky portion. And, the method further includes either (a) moving the needle from a storage position within the housing to an injection position extending through the opening of the bottom wall in a first operation state wherein the release liner remains disposed over at least a portion of the tacky portion, or (b) removing the release liner to expose the tacky portion and define a second operation state, and moving the needle from a storage position within the housing to an injection position extending through the opening of the bottom wall.

BRIEF DESCRIPTION OF THE DRAWINGS

The above needs are at least partially met through provision of the embodiments described in the following detailed description, particularly when studied in conjunction with the drawings, wherein.

DETAILED DESCRIPTION

Figure 1:
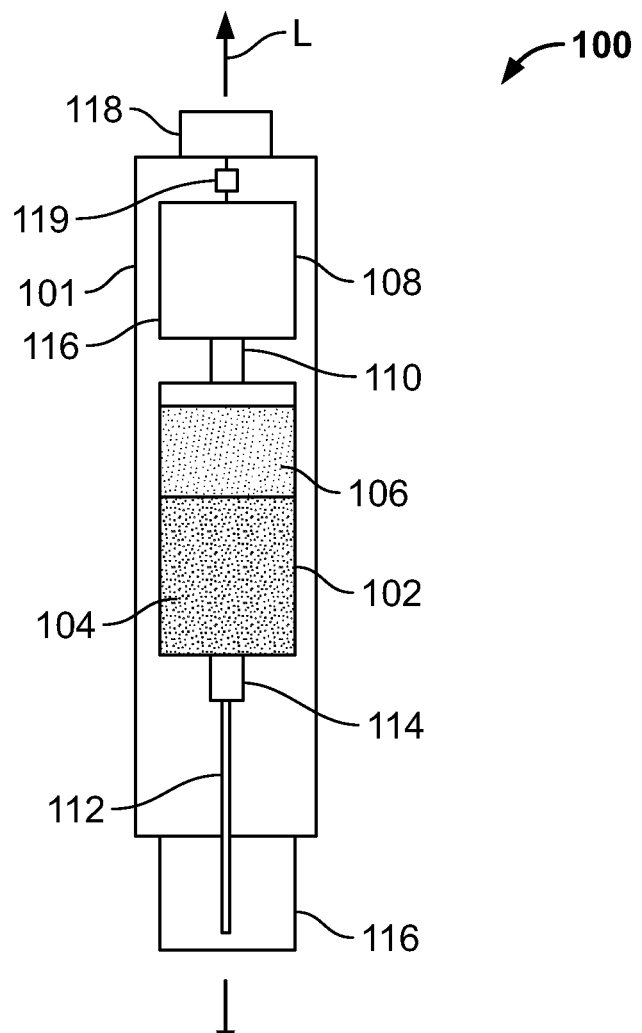
FIG. 1 is a diagrammatic view of an autoinjector drug delivery device in accordance with various embodiments.

The examples disclosed herein relate to delivery devices referred to as autoinjectors or hybrid autoinjectors that are structured to fit the lifestyle of some users better than some known and conventional autoinjectors or wearable on-body injectors devices. As such, based on the structure of the disclosed delivery devices, users can choose the interaction they have with the delivery device that is convenient for them. For example, a user can choose to perform an injection procedure in an assisted manner. Alternatively, a user can choose to rely entirely on a manual holding of the delivery device while the injection procedure is being performed. In some examples, to stabilize the delivery device relative to the body when an injection procedure is being performed, the delivery device includes an optional gripping aid for positioning and holding the devices against an intended portion of skin. The gripping aid can utilize a reduced strength adhesive so that the devices can provide aid to a user holding the device rather than being capable of hands-free operation. The gripping aid can alternatively utilize a non-adhesive tacky material and/or textured surface.

The example delivery devices can be structured to be easily held by a user with dexterity or strength challenges to substantially ensure that the injection completes successfully by increasing the grip and/or handle size of the delivery device. Put another way, the form factor of the disclosed delivery devices can be structured to be more easily held in place against the skin during an injection procedure. Furthermore, because the form factor of the disclosed examples is different than some known delivery devices, users may feel less stigma using the example devices because the delivery devices may be less recognizable as a drug delivery device.

Additionally or alternatively, the example delivery devices are structured to increase a foot print and/or increase the surface area interacting with the skin of the user during an injection procedure to increase stability of the delivery device. As such, the examples disclosed herein enable less adhesive, reduced strength adhesive and/or no adhesive to be used when stabilizing the delivery devices relative to the skin. Reducing and/or eliminating the use of adhesives is especially beneficial for users with thin skin or other skin issues where adhesives may cause negative reactions (e.g., pain, a rash).

In some versions, the drug delivery devices have generally co-axial drug delivery components such that some or all of a drug reservoir, plunger mechanism, and needle are axially aligned. The drug delivery devices described herein having this configuration provide stability, gripping, and/or adhesion functionalities typically associated with low profile drug delivery devices to aid users in orienting and supporting the device during an injection operation. As a more specific example, drug delivery devices of this form may include a housing for the co-axial drug delivery components having a skin contact surface that extends generally transverse to the axis of the drug delivery components. If desired, the skin contact surface can advantageously be utilized to support one or more retention materials that can aid a user in holding the device on the skin. The retention materials can be any non-slip texture or material, and/or adhesive.

In other versions, the drug delivery devices can have a low profile configuration with a drug reservoir having a longitudinal axis that extends generally orthogonal to an axis of a needle and/or cannula. The drug delivery devices having this configuration described herein can provide a user with multiple potential operation states including a state providing exposed retention materials to aid a user in holding the device on the skin and a state with the retention materials covered.

In some versions as illustrated in FIG. 1, drug delivery devices 100, such as autoinjectors, can have a vertically oriented configuration with some or all drug delivery components disposed in stacked relation along a longitudinal axis L within a housing 101 of the devices 100. As a more specific example, the devices 100 can be configured to operate and inject a user with the device 100 oriented generally perpendicular to a skin surface of the user. The drug delivery components can include a reservoir 102 having a drug 104 contained therein, a stopper 106 disposed within the reservoir 102 and sildably movable therein along the longitudinal axis L, a drive mechanism 108 coupled to a plunger 110 to drive the stopper 106 through the reservoir 102, a needle 112 oriented along the longitudinal axis L, a flow path 114 fluidly coupling the reservoir 102 to the needle 112, and a needle insertion mechanism 116 configured to insert the needle 112 to a desired subcutaneous depth within the user. By some approaches, the needle insertion mechanism 116 can be a retractable needle guard to expose the needle 112 or a drive mechanism to longitudinally move the needle a desired distance. For example, the drive mechanism 108 can be configured to drive both movement of the stopper 106 and the needle 112 by moving some or all of the reservoir 102, flowpath 114, and needle 112. As commonly configured, one or more of the components of the device 100, such as the drive mechanism 108 and needle insertion mechanism 116, can be operable in response to actuation of a user input device 118 accessible on an exterior of the housing 101. Suitable drive mechanisms include, but are not limited to, springs, gas sources, phase changing materials, motors, or other electromechanical systems. Pursuant to this, the device 100 can include electronic components, such as a controller 119, to control operation of one or more of the drug delivery components. It will be understood that although FIG. 1 shows the components centered along the longitudinal axis L, one or more of the components can be disposed off center from the longitudinal axis L within the housing 101 and still be considered to be in a stacked relation. In one example, an autoinjector drug delivery device having drug delivery components in a stacked relation corresponds to the reservoir 102 co-axially aligned with the needle 112. Example autoinjector devices are described in U.S. Ser. No. 62/447,174, filed Jan. 17, 2017, which is hereby incorporated by reference herein.

Given the stacked orientation of the components and the high-profile nature of the housing 101, the devices 100 of these versions can be prone to have a physically unstable configuration (i.e., prone to tipping over unless held by a user), relying on a user to position, orient, and hold the device 100 during an injection operation. Advantageously, devices described herein with reference to FIGS. 2 and 3, have a hybrid functionality providing aid to a user for more stability with a stable vertical orientation. Further, the devices can provide a user an option for a grip portion of the contact surface so that the devices grip the user's skin. This provides aid to users having limited dexterity who may be unable to position and hold the device 100 during an injection operation.

Figure 2:
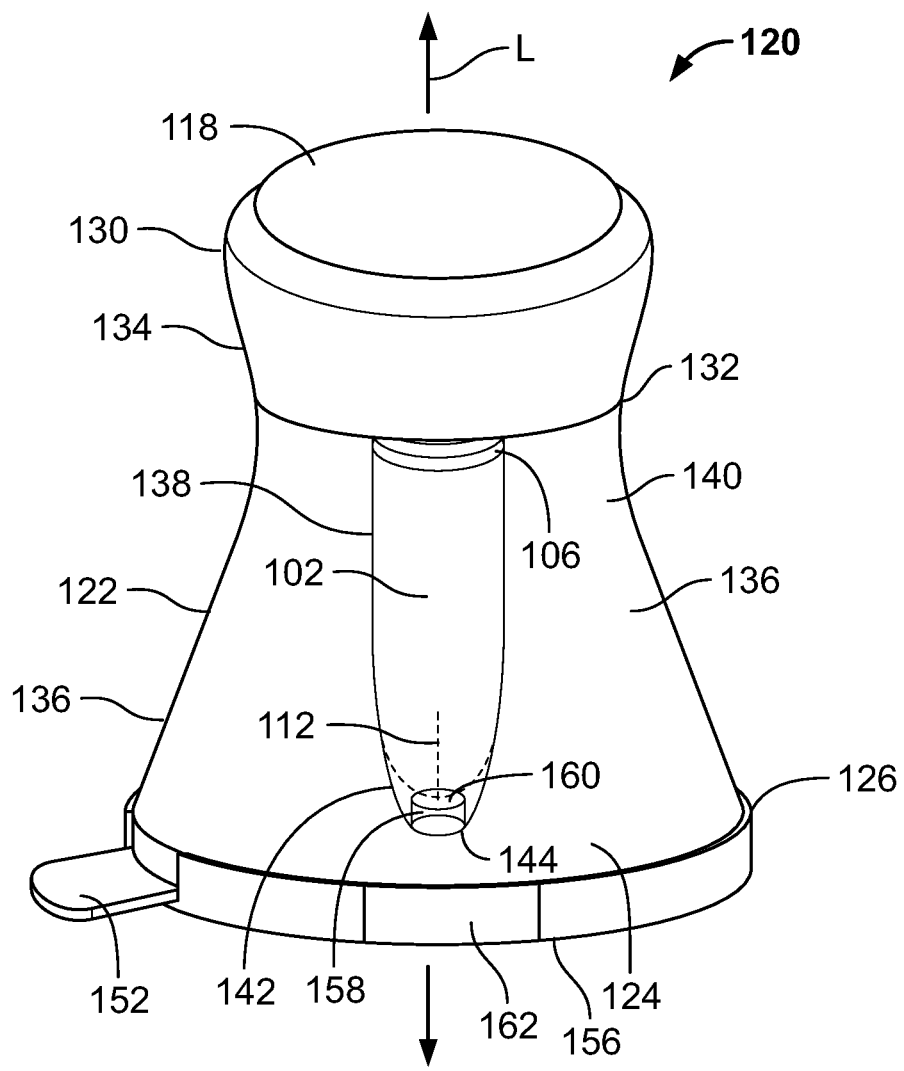
FIG. 2 is a front perspective view of an autoinjector drug delivery device in accordance with various embodiments.
Figure 3:
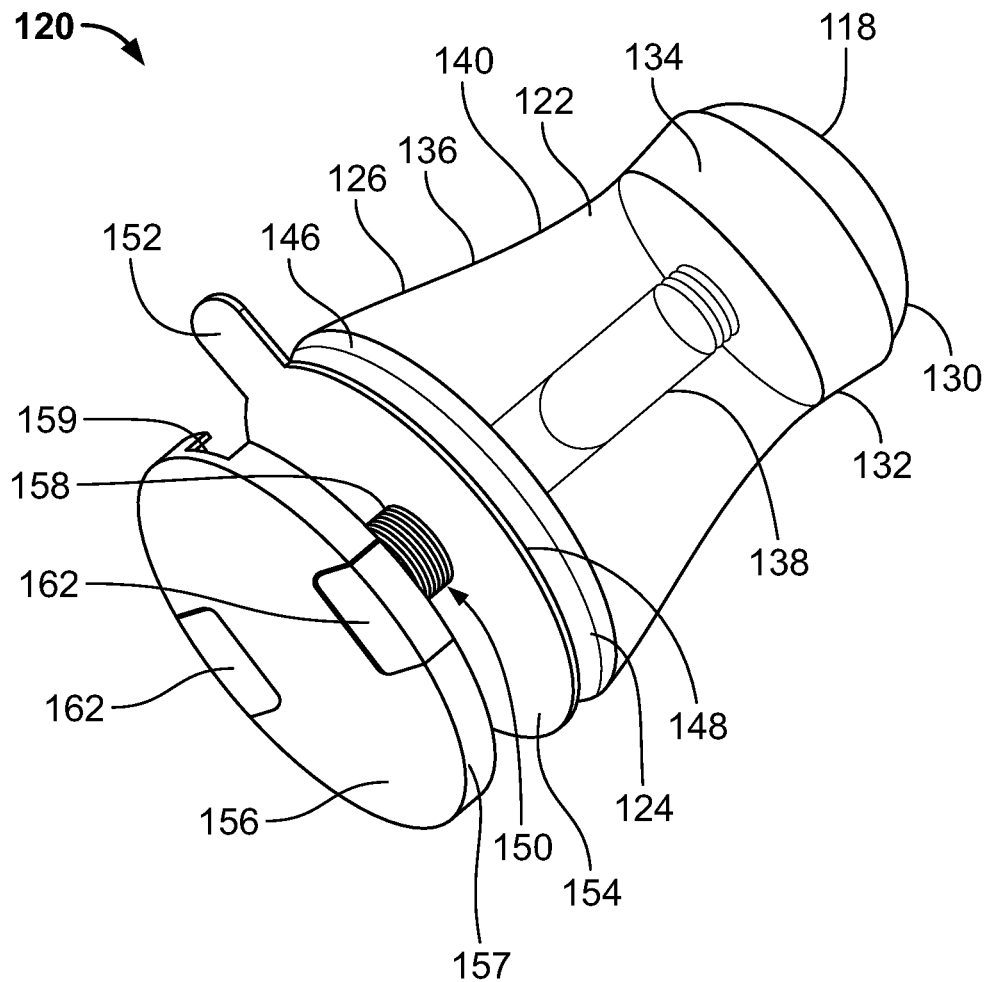
FIG. 3 is a exploded view of the autoinjector drug delivery device of FIG. 2.

One example embodiment of an autoinjector device 120 providing these features is shown in FIGS. 2 and 3. The device 120 includes a vertically oriented housing 122 oriented along a longitudinal axis L with a bottom wall 123 having a planar skin contact surface 124 at a proximal end 126 and an activation button 128 at a distal end 130. As shown, the housing 122 has an ergonomic frusto-conical configuration with a circumferential waisted portion 132 disposed between the proximal and distal ends 126, 130 to provide a gripping surface for a user.

As discussed above, conventional autoinjector devices typically have physically unstable elongate housings with the drug delivery components vertically stacked therein. In order to provide a stable vertical orientation, the skin contact surface 124 of this embodiment has a dimension, e.g., a circumference, at least half a height of the housing 122, and preferably, about ⅔ of a height of the housing 122. This allows the device 120 or stably rest in a vertical orientation when left on a flat surface.

If desired, the housing 122 can be divided by the waist 132 into an upper portion 134 and a lower portion 136. Given the stacked orientation of drug delivery components along the longitudinal axis L, the lower portion 136 can include an inner tubular portion 138 to house drug delivery components and an outer wall portion 140 to provide the ergonomic configuration of the housing 122 and provide the skin contact surface 124. Utilizing the inner and outer portions 138, 140 allows the housing 122 to having a compact housing for some of the drug delivery components, provide a stable base, and minimize material usage.

The inner tubular portion 138 can have a tapered, rounded, or bulleted configuration at an end 142 disposed adjacent to the skin contact surface 124 and an opening 144 extending through the bottom wall 123. This shape can provide a visual indication to a user of the correct orientation of the housing 122 during an injection operation. As shown in FIG. 2, the inner tubular portion 138 can be ideally configured to house the reservoir 102 containing the drug 104, the stopper 106 disposed within the reservoir 102, the needle 112, and the flow path 114 fluidly coupling the needle 112 and the reservoir 102. The needle 112 can be rigidly coupled to the reservoir 102, such as mounted within a throat of the reservoir 102 or within a needle hub, or movably coupled to the reservoir 102 by a flexible conduit. Further, the lower portion 134 can extend between the waist 132 and the proximal end 126 can be transparent or translucent so that a user can observe the reservoir 102, stopper 106, and needle 112 before, during, and after a drug delivery operation. Additionally, the end 142 of the tubular portion 138 can be obscured or frosted to hide an exact positioning of the needle 112.

As shown in FIG. 2, the upper portion 134 can be of an opaque material or coating to obscure the view of the drug delivery components disposed therein. The upper portion 134 can be used to house the drive mechanism 108, the plunger 110, and, if applicable, electronic components and pathways to control operation of the drive mechanism 108 in response to actuation of the user input device 118. Upon activation, the drive mechanism 108 can drive the plunger 110 through the reservoir 102 to push the stopper 106 and thereby push the drug 104 through the needle 112. As with the above embodiment described with reference to FIG. 1, the drive mechanism 108 can be axially aligned with one or more of the plunger 110, the reservoir 102, the stopper 106, and the needle 112. By other approaches, with the increased width of the upper portion 134 of the housing 122, the drive mechanism 108, and other components, can be disposed laterally adjacent to the plunger 110 or offset therefrom. It will be understood that having the drug delivery components in a stacked relation as described herein includes components disposed above and offset from the longitudinal axis L.

Further details of the skin contact surface 124 are shown in FIG. 3. For example, the skin contact surface 124 may include a tacky portion such as a coating or tape. The tacky material can be any suitable material with an optional texture, such as adhesive, silicone, and non-woven fabric. As a more specific example, the skin contact surface 124 can have an adhesive layer or coating 146 disposed thereon that extends around the needle opening 144 in an annular configuration. In the illustrated form, the adhesive extends to adjacent a side edge of the bottom wall 123. Of course, a smaller annular portion, or a plurality of discrete portions can also be utilized. The size of the adhesive 146 and/or the strength of the adhesive 146 can be optimized to provide a user with a desired functionality. For example, the size and/or strength of the adhesive 146 can be configured to aid a user in holding the device 120 in a desired location and orientation, without an adhesion associated with hands-free operation and the resulting difficult removal.

As shown in FIG. 3, a release liner 148 can be applied to cover at least a portion of the adhesive 146 on the skin contact surface 124. The release liner 148 includes an opening 150 extending therethrough that aligns with the needle opening 144 of the bottom wall 123 providing an obstruction free path for the needle 112 to pass therethrough. The release liner 148 can further include a tab 152 extending outwardly from a main portion 154 covering the skin contact surface 124 to provide a convenient grip for a user to selectively remove the liner 148.

With this configuration, the device 120 provides a user with the option of using the adhesive 146 during an injection operation. Accordingly, the device 120 has a first state of operation with the release liner 148 covering the adhesive 146 and a second state of operation with the adhesive 146 exposed to aid a user in locating, stabilizing, and supporting the device 120 on the skin.

The device 120 can further include a cap 156 that removably couples to the housing 122 to cover the skin contact surface 124 and the needle opening 144 before and after use. As shown in FIG. 3, a sidewall 157 of the cap 156 can include a gap 159 sized to receive the tab 152 therethrough. The cap 156 can further include an upwardly projecting needle shield 158 that is sized and configured to extend through the needle opening 144 to engage the needle 112 when the cap 156 is secured to the housing 122. The needle shield 158 can protect the needle 112 during storage and transportation. If desired, the cap 156 may be configured to maintain sterility within the device 120 and/or the needle 112 can be embedded within the needle shield 158 to maintain closed container integrity (CCI) prior to an initial removal of the cap 156. In some versions, the needle shield 158 can have a funneled upper surface 160 to locate and direct the needle 112 into a desired orientation when the needle shield 158 is inserted through the opening 144. In an alternative form, the needle shield 158 can instead couple to a needle shield preinstalled in the device 100, such that removal of the cap 156 also removes the separate needle shield.

The cap 156 can secure to the housing 122 by any suitable mechanism. In the illustrated example, the cap 156 includes inwardly displaceable catch members 162 disposed in opposing radial positions across the cap 156. The catch members 162 can operate similar to a camera lens cap to slide catches radially inwardly. Thereafter, the cap 156 can be mounted to the housing 122 and the catch members 162 released so that the catches slide radially outwardly to engage the housing 122 to secure the cap 156 thereto. Of course, other mechanisms can alternatively be utilized, such as snap-fit, threading, tongue-and-groove, and so forth.

Figure 4:
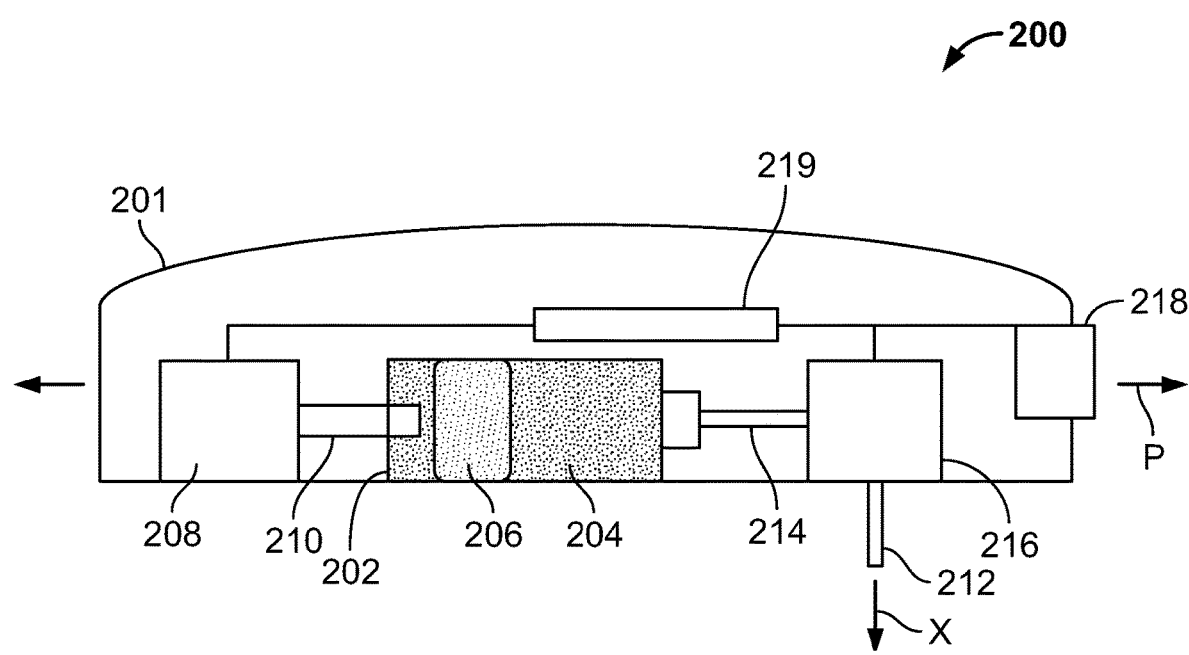
FIG. 4 is a diagrammatic view of an on-body injector drug delivery device in accordance with various embodiments.

In other versions, as illustrated in FIG. 4, drug delivery devices 200, such as on body injectors, can have a horizontally oriented configuration with drug delivery components disposed generally along a horizontal plane P within a housing 201 of the devices 200. With these devices 200, the housing 201 has a low profile with a larger width than height so that when a user positions the housing 201 on the skin, the components are spread out over an area of the skin rather than stacked as with the above embodiments. The drug delivery components can include a reservoir 202 having a drug 204 contained therein, a stopper 206 disposed within the reservoir 202 and sildably movable therein along the horizontal plane P, a drive mechanism 208 coupled to a plunger 210 to drive the stopper 206 through the reservoir 202, a needle 212 oriented along an axis X that extends generally perpendicular to the horizontal plane P, a flow path 214 fluidly coupling the reservoir 202 to the needle 212, and a needle insertion mechanism 216 configured to insert the needle 212 to a desired subcutaneous depth within the user. As commonly configured, one or more of the components of the device 200, such as the drive mechanism 208 and needle insertion mechanism 216, can be operable in response to actuation of a user input device 218 accessible on an exterior of the housing 201. Pursuant to this, the device 200 can include electronic components, such as a controller 219, to control operation of one or more of the drug delivery components. Of course, it will be understood that some components can be disposed partially or entirely above or below the horizontal plane P extending generally centrally through the housing 201 and still be considered to have a horizontally oriented configuration. Suitable drive mechanisms include, but are not limited to, springs, gas sources, phase changing materials, motors, or other electromechanical systems. Example on body injector devices are described in U.S. Ser. No. 62/536,911, filed Jul. 25, 2017, which is hereby incorporated by reference herein.

Given the spread out, horizontal orientation of the components and the low-profile nature of the housing 201, the devices 200 of these versions have a relatively large skin contact area, which is used by conventional devices for an adhesive to adhere the on body injector to the skin of the user for subsequent hands-free operation. Advantageously, devices described herein with reference to FIGS. 5-11, have a hybrid functionality optionally providing aid to a user with an adhesive contact surface so that the devices grip the user's skin. This provides aid to users having limited dexterity who may be unable to position and hold the device 200 during an injection operation without resorting to hands-free operation.

Figure 5:
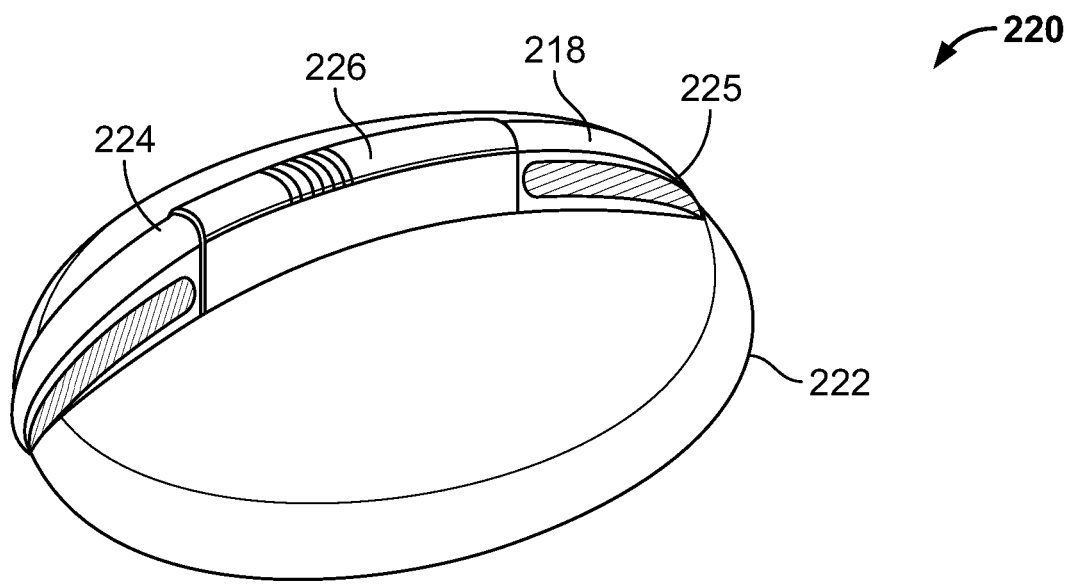
FIG. 5 is a perspective view of an on-body injector drug delivery device in accordance with various embodiments.
Figure 6:
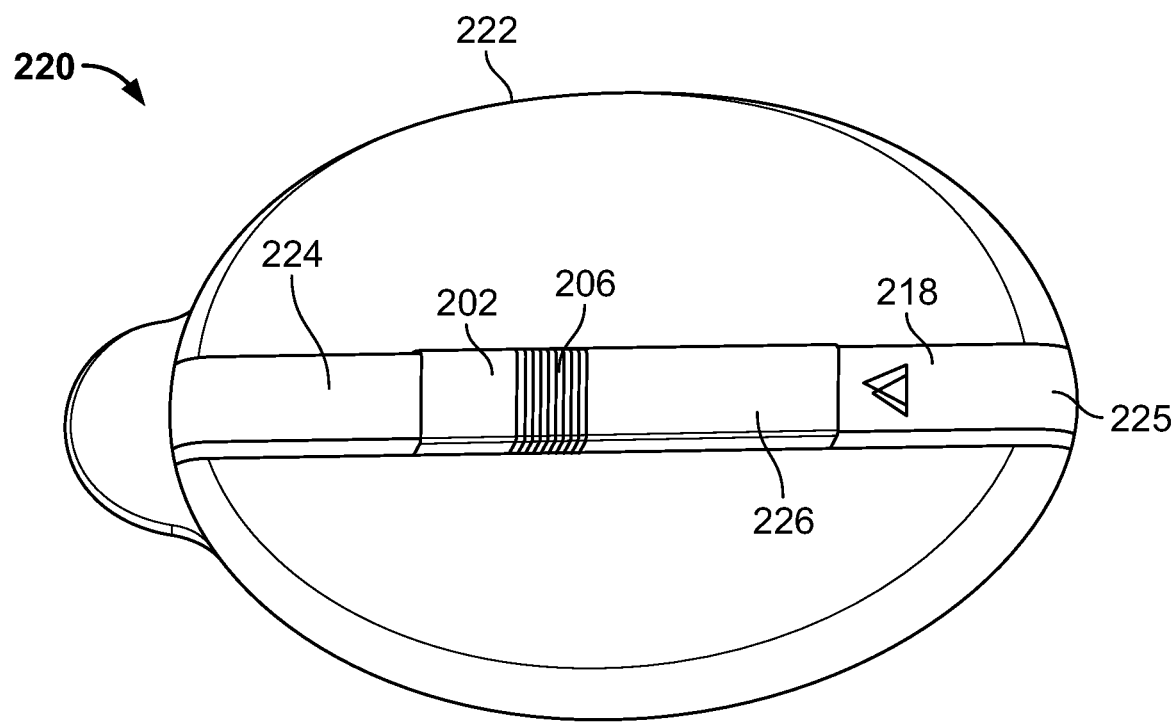
FIG. 6 is a top plan view of the on-body injector drug delivery device of FIG. 5.
Figure 7:
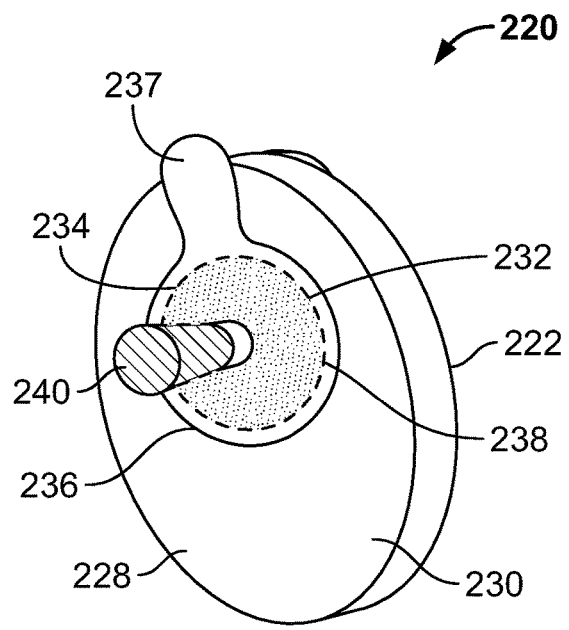
FIG. 7 is a bottom perspective view of a first embodiment of a grip portion and liner for the on-body injector drug delivery device of FIG. 5.

One example of an on-body injector 220 is shown in FIGS. 5 and 6. The injector 220 includes a housing 222 having a domed profile intended to be ergonomic for a user's hand to lay thereacross as shown in FIG. 7. A raised central ridge 224 extends along a length of the housing 222 and can include a button portion 218 at an end 225 thereof and/or an intermediate window portion 226. A user can selectively depress the button 218 to operate the injector 220 and can view a status of the injection operation through the window 226 by observing the progress of the stopper 206 and the plunger 210 being driven through the reservoir 202 (not shown).

Figure 8:
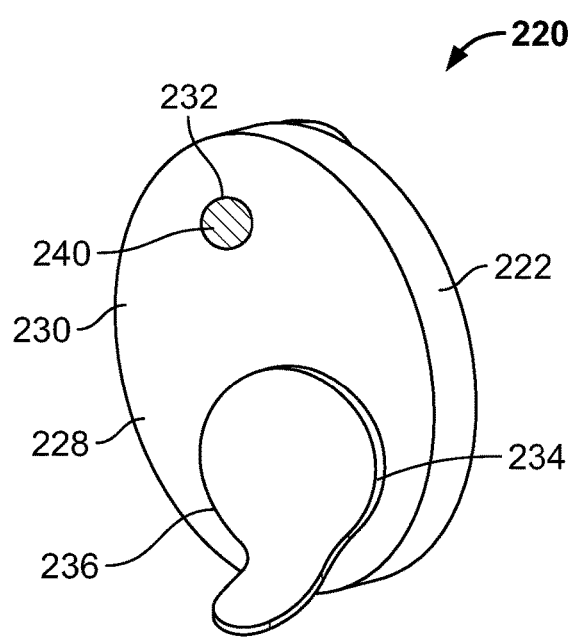
FIG. 8 is a bottom perspective view of a second embodiment of a grip portion and liner for the on-body injector drug delivery device of FIG. 5.
Figure 9:
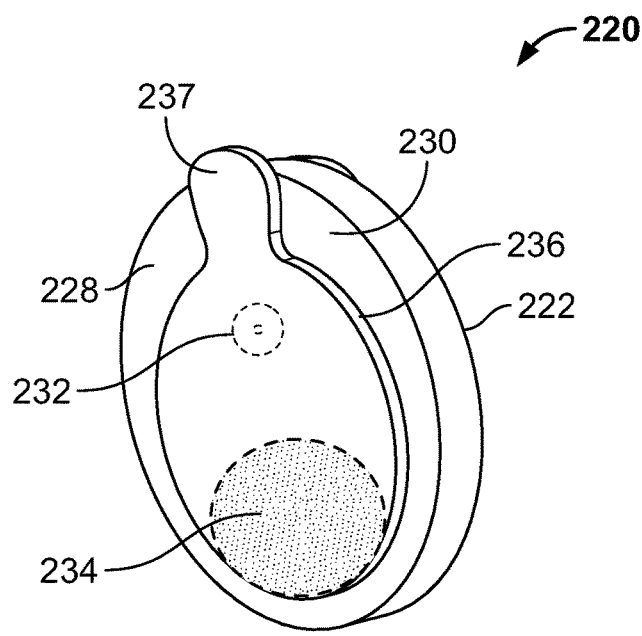
FIG. 9 is a bottom perspective view of a third embodiment of a grip portion and liner for the on-body injector drug delivery device of FIG. 5.

Example configurations for a bottom wall 228 of the injector 220 are shown in FIGS. 7-9. As shown, the bottom wall 228 includes a relatively large skin contact surface 230 that is typically associated with on-body injectors with a needle opening 232 extending therethough. Rather than an adhesive covering all or a majority of the surface 230 as with conventional designs, however, each of the illustrated embodiments includes a small tacky portion 234, which can be a coating or tape, covered by a release liner 236. The tacky material 234 can be any suitable material with an optional texture, such as adhesive, silicone, and non-woven fabric. The release liner 236 can include a gripping tab 237 to aid a user in removing the liner 236. The device 200 can be utilized with the liner 236 attached or removed so that the tacky portion 234 can aid a user in holding the housing 222 against the skin. In some examples, the tacky portion 234 can have a size less than half of the skin contact surface 230, less than a third of the skin contact surface 230, and about a fourth of the skin contact surface 230. In additional or alternative approaches, the strength of the tacky portion 234 can be moderated to aid a user in holding the device 120 in a desired location and orientation, without an adhesion associated with hands-free operation and the resulting difficult removal.

In a first embodiment shown in FIG. 7, the tacky portion 234 has an annular configuration that extends around the needle opening 232 and the liner 236 includes an opening 238 that is aligned with the needle opening 232. A needle shield 240 can then be inserted through the openings 232, 238 to engage the needle (not shown) and maintain sterility of the injector prior to use. In a second embodiment shown in FIG. 8, the needle opening 232 can be spaced from the tacky portion 234 and the liner 236 can be sized to have an similar shape and size as the tacky portion 234. If desired, a septum 240, made of a suitable elastomer material for example, can extend over of the needle opening 232 to maintain sterility until use is desired. Upon operation of the device 200, the needle (not shown) can pierce the septum 240. Alternatively, a needle shield can be inserted through the opening 232 to maintain sterility of the injector 220. In a third embodiment shown in FIG. 9, the needle opening 232 can be spaced from the tacky portion 234, but the liner 236 can be sized to cover both the tacky portion 234 and the needle opening 232. In this form, the liner 236 can be utilized to maintain the sterility of the interior of the housing 222 and the needle.

With each of these embodiments, a user can select whether to remove the liner 236 and use the tacky portion 234 to help hold and orient the device 220 on the skin. In the embodiment of FIG. 9, a user can remove or pull back the liner 236 to expose the needle opening 232 without exposing the tacky portion 234.

Figure 10:
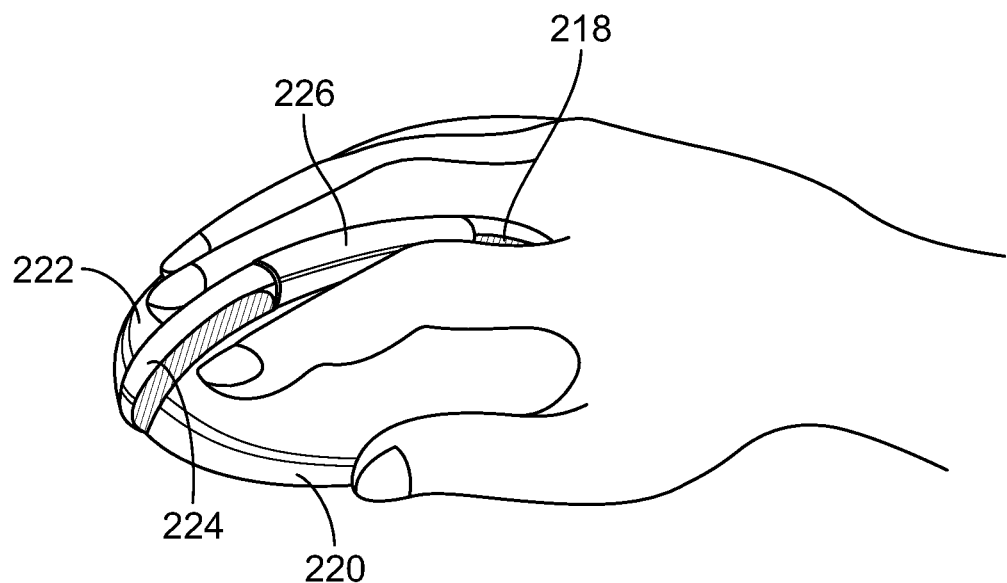
FIG. 10 is a perspective view of a user holding the on-body injector drug delivery device of FIG. 5 before and during an injection operation.
Figure 11:
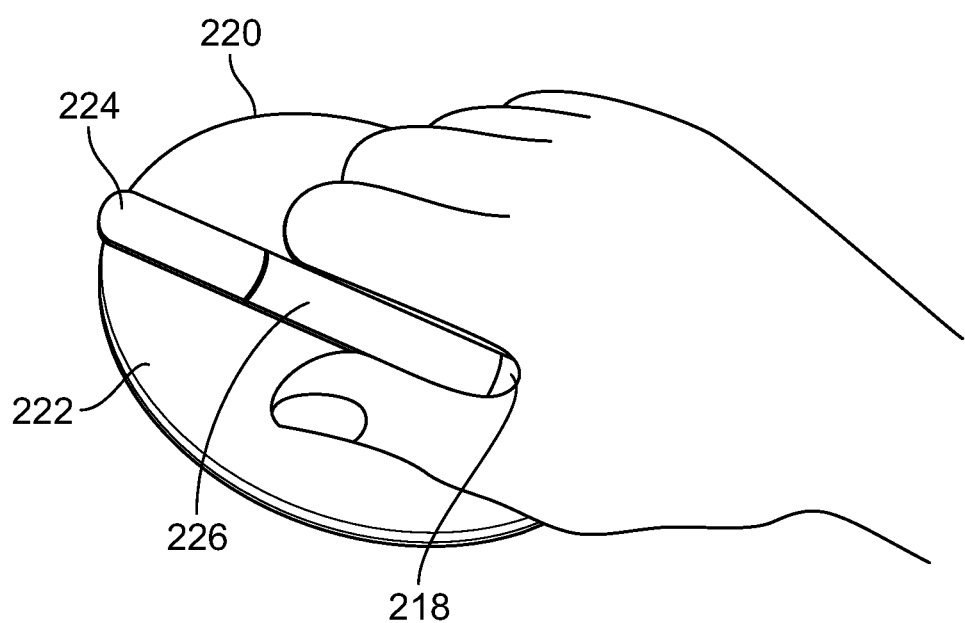
FIG. 11 is a top plan view of a user gripping the on-body injector drug delivery device of FIG. 5 for removal of the device from the skin of the user.

Devices 220 having these configurations can be handled and gripped as shown in FIGS. 10 and 11. In a first form as shown in FIG. 10 to position and hold the device 220 against the skin, a user can position a hand so that the raised ridge 224 extends between adjacent fingers on the hand. Further, the user can position a palm to at least partially cover the button 218 so that a user can easily depress the button 218 with the palm after the device 220 has been properly positioned. In a second form as shown in FIG. 11 to remove the device 220 from the skin, particularly for when a user decides to remove the liner 236, the user can grip the raised ridge 224 between a thumb and a finger to easily grip and twist the device 220 to overcome the tack of the tacky portion 234.

It will be appreciated that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. The same reference numbers may be used to describe like or similar parts. Further, while several examples have been disclosed herein, any features from any examples may be combined with or replaced by other features from other examples. Moreover, while several examples have been disclosed herein, changes may be made to the disclosed examples within departing from the scope of the claims.

The above description describes various assemblies, devices, and methods for use with a drug delivery device. It should be clear that the assemblies, drug delivery devices, or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or as a more specific example the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgrastim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS: 305-351, including TN8-19-1 through TN8-19-40, TN8-19 con1 and TN8-19 con2; peptibodies of the mL2 family of SEQ ID NOS: 357-383; the mL 15 family of SEQ ID NOS: 384-409; the mL 17 family of SEQ ID NOS: 410-438; the mL20 family of SEQ ID NOS: 439-446; the mL21 family of SEQ ID NOS: 447-452; the mL24 family of SEQ ID NOS: 453-454; and those of SEQ ID NOS: 615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1 (N); L1 (N) WT; L1 (N) 1K WT; 2×L1 (N); 2×L1 (N) WT; Con4 (N), Con4 (N) 1K WT, 2×Con4 (N) 1K; L1C; L1C 1K; 2×L1C; Con4C; Con4C 1K; 2×Con4C 1K; Con4-L1 (N); Con4-L1C; TN-12-9 (N); C17 (N); TN8-8 (N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; Ab1A1; AbIF; AbIK, AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT- 11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO: 9 respectively therein); 2H (having light chain variable and heavy chain variable sequences SEQ ID NO:3 and SEQ ID NO: 10 respectively therein); 43H (having light chain variable and heavy chain variable sequences SEQ ID NO:6 and SEQ ID NO: 14 respectively therein); 41H (having light chain variable and heavy chain variable sequences SEQ ID NO:5 and SEQ ID NO: 13 respectively therein); and 15H (having light chain variable and heavy chain variable sequences SEQ ID NO:4 and SEQ ID NO: 12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO: 17 and the light chain of SEQ ID NO: 18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO: 10 and the light chain variable region of SEQ ID NO: 12; those having the heavy chain of SEQ ID NO:32 and the light chain of SEQ ID NO:20; those having the heavy chain variable region of SEQ ID NO:30 and the light chain variable region of SEQ ID NO: 12; those having the heavy chain sequence of SEQ ID NO:21 and the light chain sequence of SEQ ID NO:22; those having the heavy chain variable region of SEQ ID NO: 14 and the light chain variable region of SEQ ID NO: 16; those having the heavy chain of SEQ ID NO:21 and the light chain of SEQ ID NO:33; and those having the heavy chain variable region of SEQ ID NO: 14 and the light chain variable region of SEQ ID NO: 31, as disclosed in the foregoing publication. A specific antibody contemplated is antibody 1119 as disclosed in the foregoing U.S. publication and having a complete heavy chain of SEQ ID NO: 17 as disclosed therein and having a complete light chain of SEQ ID NO: 18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF: cMet axis (HGF/SF: c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL 13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGB mAb (MDX-1307); anti-mesothelin dsFv-PE38 conjugate (CAT-5001); anti-PD1mAb (MDX-1106 (ONO-4538)); anti-PDGFRa antibody (IMC-3G3); anti-TGFß mAb (GC-1008); anti-TRAIL Receptor-2 human mAb (HGS-ETR2); anti-TWEAK mAb; anti-VEGFR/FIt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223, 593 and 7,537,924); OncoVEXGALV/CD (U.S. Pat. No. 7,981,669); OrienX010 (Lei et al. (2013), World J. Gastroenterol, 19:5138-5143); G207, 1716; NV1020; NV12023; NV1034 and NV1042 (Vargehes et al. (2002), Cancer Gene Ther., 9 (12): 967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BiTE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug delivery devices, methods, and elements thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention. For example, components described herein with reference to certain kinds of drug delivery devices, such as on-body injector drug delivery devices or other kinds of drug delivery devices, can also be utilized in other kinds of drug delivery devices, such as autoinjector drug delivery devices.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A drug delivery device comprising:
   a housing having a bottom wall and an opening extending therethrough, wherein the housing extends along a longitudinal axis that is generally perpendicular to the bottom wall, the bottom wall having a dimension extending thereacross that is between about one half and two thirds of a total height of the housing along the longitudinal axis;
   drug delivery components disposed within the housing including a needle having a storage position within the housing and an injection position extending through the opening of the bottom wall;
   a tacky portion disposed on the bottom wall and being configured to grip skin of a user;
   a release liner disposed over at least a portion of the tacky portion; and
   a cap removably coupled to the housing to cover the bottom wall, the tacky portion, and at least a portion of the release liner,
   the cap being entirely decoupled from the release liner such that the release liner remains disposed over at least the portion of the tacky portion upon removal of the cap from the housing,
   wherein the drug delivery components have a first potential operation state with the release liner disposed over at least the portion of the tacky portion and a second potential operation state with the release liner removed to expose the tacky portion.

2. The drug delivery device of claim 1, wherein the drug delivery components are disposed in the housing such that at least a plurality of the drug delivery components are disposed in a generally stacked relation along the longitudinal axis.

3. The drug delivery device of claim 1, wherein the housing includes a transparent portion providing visibility to drug delivery components disposed within the transparent portion.

4. The drug delivery device of claim 1, wherein the housing includes an inner tubular portion having one or more of the delivery components disposed therein aligned with the opening in the bottom wall and an outer wall spaced from the inner tubular portion in a direction perpendicular to the longitudinal axis.

5. The drug delivery device of claim 4, wherein the inner tubular portion extends to the bottom wall at an end thereof, the end having a tapered or bulleted configuration extending to edges of the opening of the bottom wall.

6. The drug delivery device of claim 1, wherein the tacky portion has an annular configuration extending around the opening in the bottom wall.

7. The drug delivery device of claim 1, wherein the cap includes a needle shield sized to extend through the opening in the bottom wall to engage the needle with the cap coupled to the housing.

8. The drug delivery device of claim 1, wherein the cap includes a sidewall extending generally parallel to the longitudinal axis of the housing and the release liner includes an outwardly protruding tab, the sidewall of the cap having a gap therein sized to receive the tab of the release liner therethrough with the cap coupled to the housing.

9. The drug delivery device of claim 1, wherein the cap entirely covers the bottom wall when the cap is removably coupled to the housing.

10. A method of preparing a drug delivery device prior to injecting a patient with a drug, the method comprising:
    providing a housing having a bottom wall and an opening extending therethrough, drug delivery components including a needle disposed within the housing, the bottom wall of the housing having a tacky portion and a release liner disposed over at least a portion of the tacky portion, wherein the housing extends along a longitudinal axis that is generally perpendicular to the bottom wall, the bottom wall having a dimension extending thereacross that is between about one half and two thirds of a total height of the housing along the longitudinal axis;
    providing a cap coupled to the housing to cover the bottom wall, the tacky portion, and at least a portion of the release liner;
    removing the cap from the housing, while the release liner remains disposed over at least the portion of the tacky portion; and
    moving the needle from within the housing through the opening of the bottom wall and through the release liner.

* * * * *